United States Patent [19]

Lerman

[11] Patent Number: 4,635,626

[45] Date of Patent: Jan. 13, 1987

[54] PROSTHETIC STOCKINGS

[76] Inventor: Max Lerman, 1950 Carla Ridge, Beverly Hills, Calif. 90210

[21] Appl. No.: 672,408

[22] Filed: Nov. 16, 1984

[51] Int. Cl.⁴ .................. A61F 13/00; B32B 25/00; B32B 7/02
[52] U.S. Cl. .................. 128/165; 128/156; 128/158; 428/40; 428/165; 428/212
[58] Field of Search .................. 128/156, 158, 165; 428/40, 165, 212

[56] References Cited

U.S. PATENT DOCUMENTS

| | | | |
|---|---|---|---|
| 2,696,011 | 12/1954 | Galdik | 3/17 R |
| 2,714,771 | 8/1955 | Olfene | 36/9 A |
| 3,180,335 | 4/1965 | Duncan et al. | 128/287 |
| 3,186,006 | 6/1965 | Miller | 128/165 |
| 3,315,676 | 4/1967 | Cooper | 128/287 |
| 3,600,717 | 8/1971 | McKeehan | 128/165 |
| 3,842,832 | 10/1974 | Wideman et al. | 128/156 |
| 3,991,424 | 11/1976 | Prahl | 128/165 |

FOREIGN PATENT DOCUMENTS 1076560  10/1967  United Kingdom .................. 3/19

Primary Examiner—Herbert S. Cockeram
Attorney, Agent, or Firm—Christie, Parker & Hale

[57] ABSTRACT

A temporary post-operative stump sock for amputees comprises a flexible, resilient composite material including a base layer of a flexible, resilient open cell material; a skin-protecting first layer of a soft, flexible porous material overlying a first face of the base layer, and a second layer of a protective fabric overlying a second face of the base layer. The composite material is cut, overlaid and seamed to form a tubular sock which is open at its top, closed at its bottom and along its sides and shaped generally to conform to the shape of the amputee's stump. The stump sock is applied to the stump, after which a socket portion of the temporary prosthesis is wrapped around the stump to make the patient ambulatory within a short period after the amputation. Another embodiment of the invention provides a permanent stump sock comprising a flexible, resilient composite material which includes a base layer of a flexible, resilient open cell elastomeric material, and first and second layers of a flexible, stretchable protective fabric adhered to opposite sides of the elastomeric layer. The composite material is cut, overlaid and seamed to form a tubular sock. In both embodiments, one or more of the outer stretchable layers of fabric can have greater elasticity laterally than longitudinally. In one technique for treating an amputee, the stump sock is formed with a volume less than the volume of the amputee's permanent stump so that the stump sock can be stretched when applied to the stump to maintain the stump in circumferential compression during use.

31 Claims, 7 Drawing Figures

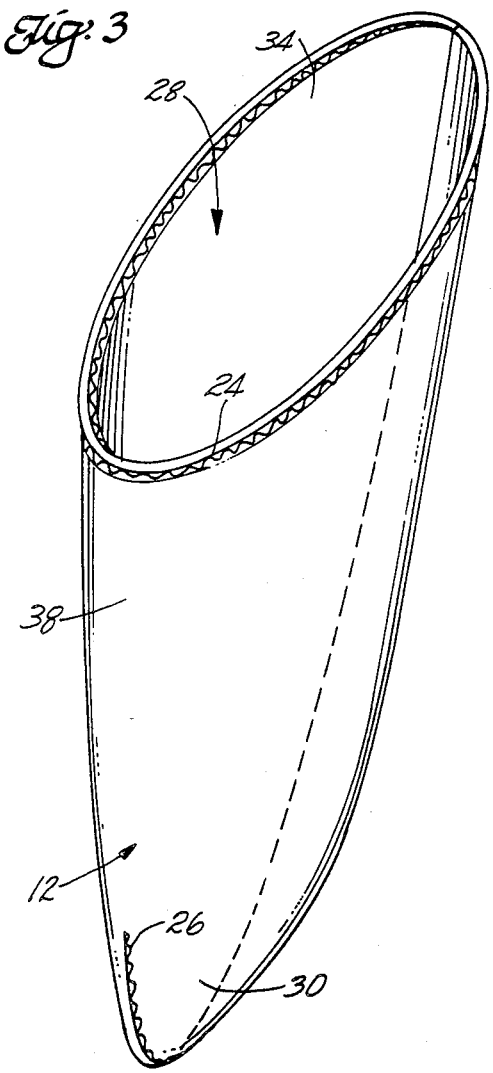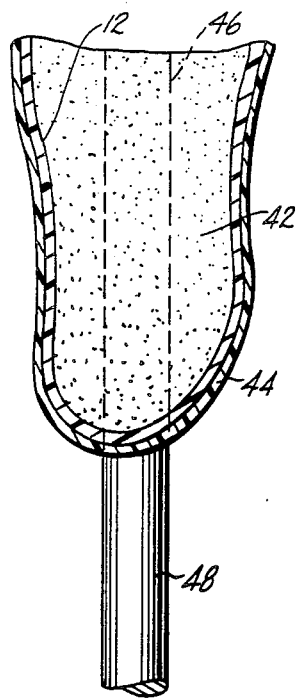

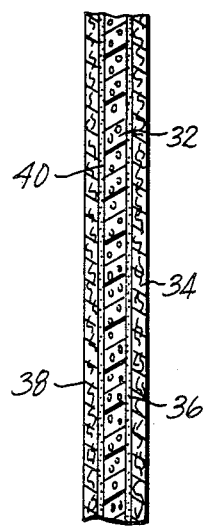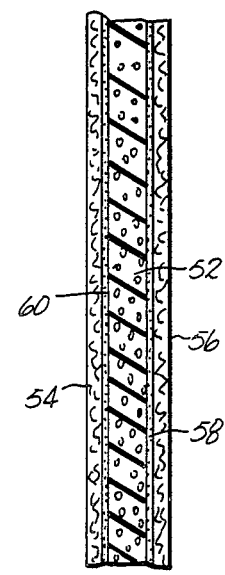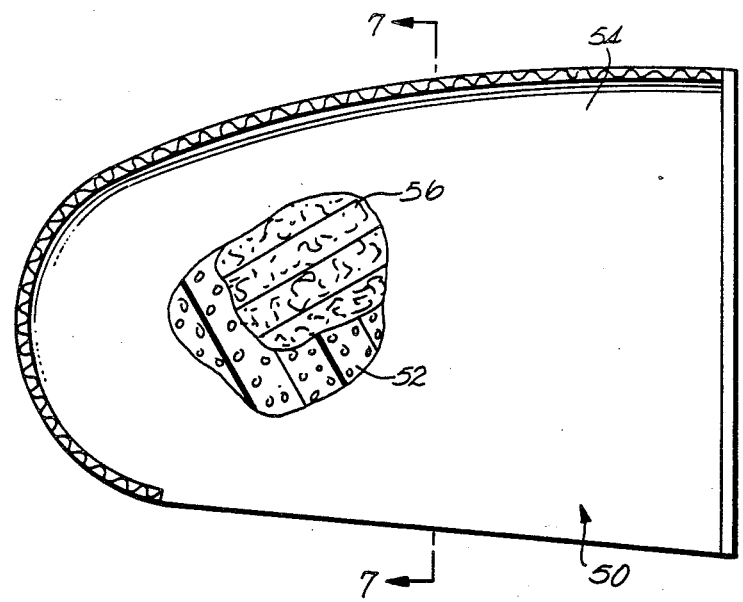

PROSTHETIC STOCKINGS

FIELD OF THE INVENTION

This invention relates to stump socks used to protect the skin of an amputee from direct contact with the prosthetic appliance. More particularly, the invention relates to both a post-operative stump sock used for a limited time with a temporary prosthesis while the amputation undergoes the healing process, and a permanent stump sock of different construction used with the permanent prosthesis after healing is completed.

BACKGROUND OF THE INVENTION

After an amputation, the stump which remains is commonly protected by a stocking or liner to shield the skin from direct contact with the prosthesis. Within one to two weeks after the amputation, a post-operative prosthesis can be worn temporarily, perhaps for a period of about two weeks to about two months. During this time the stump heals, swelling reduces, and the stump ultimately takes its final shape. It is common practice during this early post-operative period to apply a thin stocking of knitted fabric to the stump, along with one or more outer layers of padding wrapped around the stump. Common wrapping materials used for this purpose are a resilient foam or felt, or a similar material known by the trademark Webril. Over this outer layer is wrapped a rigid dressing of plaster or other similar synthetic materials to form a rigid socket for a temporary prosthesis. A pylon and prosthetic foot are attached to the socket for form the temporary prosthesis, which enables the patent to become ambulatory shortly after the amputation.

The technique of wrapping different types of available padding around the stump and then forming a temporary prosthetic limb around this wrapping is cumbersome and time-consuming. The resulting temporary prosthesis with the extraneously added padding are not always comfortable for the patient, nor is it convenient for the patient to remove and re-apply such a temporary prosthesis. In addition, there is a need to ensure that such a temporary prosthesis does not produce discomfort to the patient when the patient is ambulatory on the temporary prosthesis.

Once healing is completed, the permanent or "definitive" prosthesis is assembled by the prosthetist. The permanent prosthesis includes a stump socket made from a cast that matches the shape of the stump. A pylon attached to the stump socket carries a prosthetic foot. A liner is worn by the patient to protect the skin from direct contact with the inside of the socket. The liner is commonly form-fitted to a cast of the stump socket to match the shape of the patient's stump. One prior art liner for stump sockets is made from a material known by the trademark Pelite, a closed cell plastic foam material which has to be heat-formed on a cast to shape it to match the inside of the stump socket. Pelite is a relatively firm closed cell foam material which provides some cushioning. It also resists compression as well as twisting of the stump relative to the socket; and discomfort often can result. Another prior art liner for stump sockets is custom-made from a material known by the trademark Kemblo, a composite leather and foam rubber liner. The leather is molded onto a cast to match the inside shape of the stump socket. The rubber is then glued onto the leather liner in strips. It requires several hours for the prosthetist to make a liner by this process.

The process of custom molding a liner for the definitive prosthesis is time-consuming and expensive. Moreover, this cost is amplified because these liners wear out and require replacement by further custom-made liners. Further, if the patient gains or loses weight the volume of the stump changes; so there is an ongoing need to provide a liner that accurately and comfortably fits between the stump and socket of the permanent prosthesis.

SUMMARY OF THE INVENTION

Briefly, one embodiment of the invention provides a stump sock for temporary post-operative use comprising a flexible, resilient composite material which includes a base layer of a flexible, resilient open cell material; a skin-protecting first layer of a soft, flexible porous material overlying a first face of the base layer; and a protective second layer of a flexible fabric overlying a second face of the base layer. The composite material is cut, overlaid and seamed to form a tubular sock which is open at its top, closed at its bottom, and shaped to generally conform to the shape of an amputee's stump, with the skin-protecting first layer on the inside of the sock and the protective second layer on the outside of the sock.

The temporary stump sock can be made in a few standard sizes which eliminates the need for custom wrapping cushioning materials around the stump. The patient also can be ambulatory shortly after the amputation because the temporary stump sock facilitates fabrication of a temporary prosthesis. The socket for a temporary prosthesis is simply wrapped around and in direct contact with the temporary stump sock, after which the pylon and the foot are attached to the socket to form the temporary prosthesis. Other advantages also are provided.

Another embodiment of the invention provides a permanent stump sock comprising a flexible, resilient composite material which includes a base layer of a flexible, resilient elastomeric material, and first and second layers of a flexible and stretchable protective fabric adhered to opposite sides of the elastomeric layer. The composite material is cut, overlaid and seamed to form a tubular sock which is open at its top, closed at its bottom, and shaped to generally conform to the shape of an amputee's stump.

The permanent stump sock can be made in a few standard sizes and eliminates the need for custom molding a protective liner for the stump socket of the permanent prosthesis. The permanent stump sock also is stretchable and can be made to provide an effective means of serving as a compression stocking to inhibit swelling during use. The materials from which the permanent stump sock is made also combine to provide a low friction material which enhances comfort as well as providing cushioning and compression.

These and other aspects of the invention will be more fully understood by referring to the following detailed description and the accompanying drawings.

DRAWINGS

FIG. 3 is a perspective view showing the temporary stump sock.

FIG. 4 is a fragmentary, schematic cross-sectional view taken on line 4—4 of FIG. 2.

FIG. 5 is a fragmentary, semi-schematic elevation view, partly in cross-section, illustrating the temporary stump sock in use on a temporary prosthesis.

FIG. 6 is an elevation view, partly in cross-section, showing a permanent stump sock.

FIG. 7 is a fragmentary, schematic cross-sectional view taken on line 7—7 of FIG. 6.

DETAILED DESCRIPTION

Figure 1:
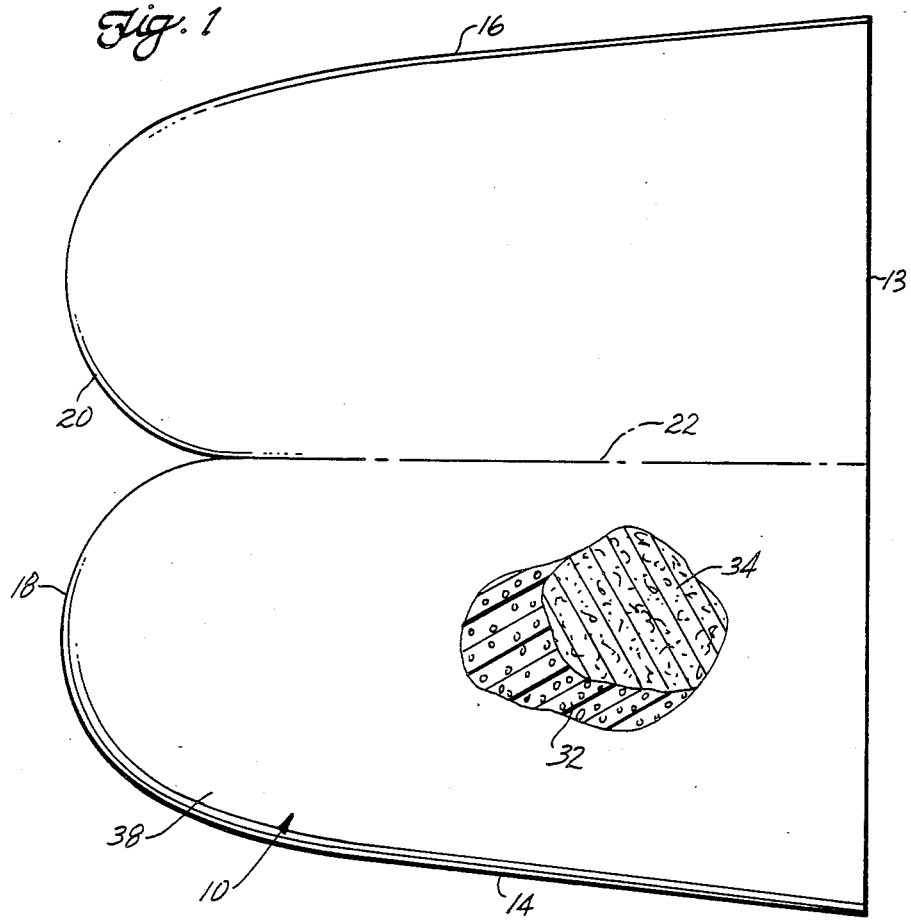
FIG. 1 is an elevation view, partly in cross-section, showing a temporary stump sock in flat form.

FIGS. 1 through 4 illustrate a temporary stump sock according to principles of this invention. The temporary stump sock provides temporary cushioning for the stump remaining after a below-knee amputation. The temporary stump sock is used for a short post-operative period of about two weeks to about two months after the amputation, during the healing process. The temporary stump sock is made from a flexible, resilient composite material 10 shown in flat form in FIG. 1. The flat form composite layer of FIG. 1 is foled over and seamed to form a finished temporary stump sock 12 illustrated in FIGS. 2 and 3.

Figure 2:
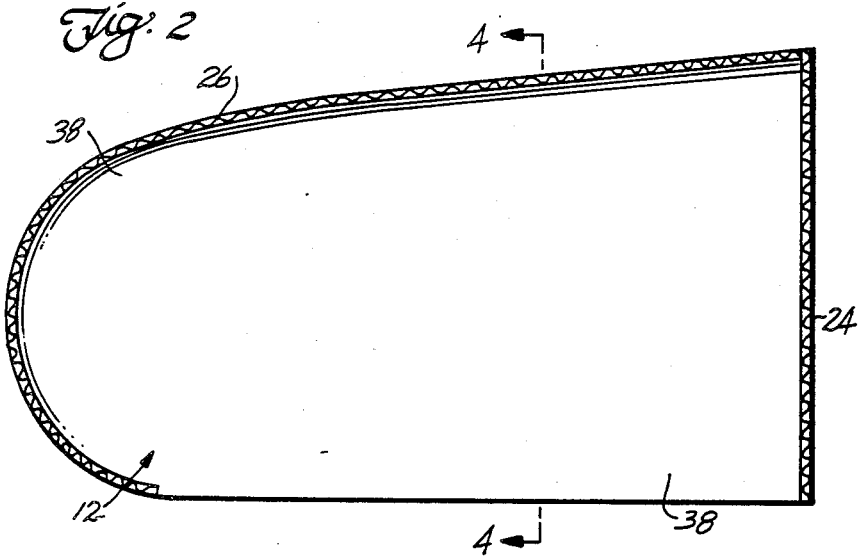
FIG. 2 is a side elevation view showing a completed temporary stump sock.

Referring to FIGS. 1 and 2, the composite material 10 is cut in flat form to provide a straight top edge 13, tapered first and second side edges 14 and 16 which converge slightly toward each other in a direction away from the top edge, and first and second U-shaped bottom edges 18 and 20 which meet at the bottom of a straight central fold line 22 shown in phantom lines in FIG. 1. The flat form material illustrated in FIG. 1 is cut in a pattern that is symmetrical about the imaginary dividing fold line 22. The composite material 10 has a continuous stitched seam 24 extending along its top edge. The side edges 14, 16 and bottom edges 18, 20 also have a continuous stitched seam 26. The composite material is folded along the fold line 22 so that half of the flat form composite layer overlies the other half. The outer peripheries of the overlapping composite layer sections are then secured together by a continuous seam which extends from the bottom of the fold line 22 around the U-shaped edges 18 and 20 and along the tapered outer edges 14 and 16 to the top edge 13. This forms the finished stump sock 12 illustrated in FIGS. 2 and 3, which is generally tubular in shape, having an open top 28, a closed bottom 30, and a continuous closure that tapers along the side from the open top to the closed bottom.

The materials which comprise the composite material 10 are understood best by referring to the schematic view of FIG. 4. The composite material includes a base layer 32 of a flexible, resilient open cell material. The preferred open cell material is a high density polyester foam. The preferred a high density polyester foam has a density of at least about 6 pounds per cubic inch with an uncompressed uniform layer thickness of about ¼ inch. A base layer of the same thickness with a density of less than about 6 pounds per cubic inch, does not provide the necessary strength to resist bottoming out of the stump sock during use. The open cell foam material is used because it "breathes", i.e., it is porous to air and water. Such a material is used to ensure good air circulation to the stump and good dissipation of heat and absorption of fluids during the healing process.

The composite layer also includes a soft, flexible and somewhat compressible inner layer 34 of a material which is also porous to air and water. The presently preferred material is velour. In the flat form stump sock illustrated in FIG. 1, the inner layer 34 overlies the compressible base layer 32 and the two layers are adhered by surface contact by an adhesive layer 36. A conventional spray-on adhesive provides the desired surface adhesion over the entire surface areas of the adjoining layers 32 and 34.

The composite material 10 also includes a protective outer layer 38 of a flexible and stretchable cloth. The preferred outer layer is known by the trademark Tricot. This material is porous to air and water. The flexible outer layer preferably has different elasticity or stretchability in mutually orthogonal directions. In the preferred stump sock, the outer layer 38 is arranged so it has greater stretchability laterally, i.e., across the sock in a direction generally parallel to its top edge 13, while the outer layer has limited longitudinal stretchability, i.e., the resulting stump sock has greater elasticity laterally and has more resistance to stretching longitudinally, i.e., perpendicular to its top edge 12. The preferred protective outer layer also is a material which is porous to air and water. The outer layer 38 is cut into the same form as that shown in FIG. 1 and overlies the compressible base layer 32. The two layers are adhered to one another by an adhesive layer 40 similar to adhesive layer 36. The adhesive layer 40 provides a means of surface adhesion between the layers 32 and 38 uniformly across the entire area of surface contact. Since the outer layer 38 of stretchable fabric provides a completed stump sock with more stretchability laterally than longitudinally, it facilitates fitting the sock onto the stump. The greater resistance to stretching in the longitudinal direction inhibits loss of elastic properties of the sock during use and provides good support for the tissues during use.

When the composite material is cut into the form illustrated in FIG. 1, the size of the flat form material is dependent upon the size of the stump to be fitted. Once the flat form material is cut, stitched to provide the peripheral stitching 24 and 26, folded over along the fold line 22, and seamed along the adjacent peripheral edges to form the completed sock 12, the sock is then ready for fitting to the patient. The temporary stump sock greatly simplifies the techniques for providing a cushioned temporary prosthesis for the amputee. FIG. 5 illustrates the temporary stump sock in use on a stump 42 remaining after a below-knee amputation. After the temporary stump sock is applied to the stump, the socket portion of the temporary prosthesis is wrapped around the temporary stump sock. No extraneous padding or the like need be applied to the stump. The socket portion 44 of the temporary prosthesis can be an outer layer of plaster applied directly to the exterior of the temporary stump sock. Alternatively, the socket portion 44 of the prosthesis can be fabricated insitu by placing an upwardly opening cup-shaped section of a temporary prosthesis around the stump sock and then wrapping the upper section of the prosthesis and the exterior of the stump sock with a casting tape such as the tape sold under the trademark Scotchcast by 3M Company. The temporary prosthesis in this instance can be made from an artificial limb having separate radially offset fingers 46 at one end of an elongated pylon 48. The wrapping of casting tape adheres to the exterior of the fingers 46 and to the exterior of the stump sock to form a completed prosthesis with a cushioned upper section above the lower pylon 48. An artifical limb of the type to which the temporary stump sock 12 can be applied is disclosed in U.S. Pat. No. 4,459,709. Other means for forming the socket portion of a temporary prosthesis around the stump sock 12 also can be used.

FIGS. 6 and 7 illustrate an additional embodiment of the invention comprising a permanent stump sock 50. This stump sock is constructed in a manner similar to the stump sock illustrated in FIGS. 1 through 4, although the materials differ. That is, the stump sock 50 is made from a flexible, resilient elastomeric composite material initially made in flat form in a shape similar to that shown in FIG. 1. The layered material, after the different plies are overlaid and adhered to one another, is cut into the form illustrated in FIG. 1 and then stitched around the periphery and seamed as illustrated for the stump sock of FIGS. 2 and 3. Referring again to the permanent stump sock 50 shown in FIGS. 6 and 7, this stump sock includes a composite layer which includes a base layer 52 of a flexible, resilient elastomeric open cell material. The preferred open cell elastomeric material is sponge rubber. Alternatively, neoprene rubber can be used, but this material is a closed cell material, and open cell materials are preferred. The open cell material is porous to air and water. The flexible elastomeric base layer 52 is preferably about ⅛ to 3/16 inch thick.

A flexible, stretchable inner layer 54 and a similar flexible, stretchable outer layer 56 of fabric overlie opposite faces of the base layer 52. Separate adhesive layers 58 and 60 adhere the inner and outer layers to the elastomeric base layer 52. The flexible, stretchable outer layers 56 are preferably made from a stretchable nylon cloth or other similar knitted fabric. This material is porous to air and water. Preferably, the inner and outer layers 54 and 56 are made from a material having differeing stretchability in mutually orthogonal directions. The permanent stump sock is preferably constructed so that the inner and outer layers 54 and 56 combine to provide greater stretchability laterally and limited stretchability longitudinally. The preferred fabric for the inner and outer layers in the material known by the trademark Tricot.

The stump sock 50 is highly useful as a permanent stump sock when compared with previous molded, cast, custom-made or otherwise hand-fitted stump socks or protective cushioning devices used with permanent prostheses of the prior art. The stump sock is worn on the stump which is then placed inside the socket of the permanent prosthesis. The stump sock provides protective cushioning and is not normally adhered to the inside of the socket on the prosthesis. The stump sock eliminates the need for a separate liner for the socket of the prosthesis. The permanent stump sock of this invention can be provided to the trade in a few standard sizes. The cost of replacement of the stump sock due to excess wear is substantially less than previous stump socks which are more expensive because of their custom-made or cast fit characteristics. Moreover, the stump sock can be easily adjusted to use in various thicknesses when desired. It can easily be made for patients who gain or lose weight, when the volume of the stump changes. Further, the elasticity of the stump sock aids in suspension of the prosthesis and reduces coefficient of friction and therefore enhance comfort. The permanent stump sock provides good cushioning for the bony prominences of the user's stump. Its elasticity avoids discomforting resistance to twisting of the stump relative to the socket of the permanent prosthesis. The elastic properties of the permanent stump sock also aid in compression of the stump. The stump sock can be made slightly smaller in volume than the volume of the stump. This maintains compression which prevents swelling of the tissues during use. The greater elasticity laterally facilitates stretching the stump sock so it can be fitted onto the stump, while the resistance to stretching longitudinally provides good support for the stump during use.

What is claimed is:

1. A temporary post-operative stump sock comprising a flexible, resilient composite material including a base layer of a flexible, resilient open cell material; a skin-protecting first layer of a soft, flexible porous material overlying and adhered to a first face of the base layer; and a flexible second layer of a protective fabric overlying and adhered to a second face of the base layer, the composite material being cut, overlaid and seamed to form a tubular sock which is open at its top, closed at its bottom and shaped generally to conform to the shape of an amputee's stump, with the skin-protecting first layer on the inside of the sock and the protective second layer on the outside of the sock.

2. A stump sock according to claim 1, in which the resilient open cell base layer comprises a high density polyester foam.

3. A stump sock according to claim 1, in which the protective second layer thereof comprises a fabric with differing levels of elasticity in mutually orthogonal directions, the elasticity being greater in a lateral direction than in the longitudinal direction with respect to the length of the finished stump sock.

4. A stump sock according to claim 3, in which each layer of the composite material is porous to air and water.

5. A stump sock according to claim 4 attached to a temporary prosthetic limb having a cup-shaped upper portion surrounding the temporary stump sock and in direct contact with the exterior of the stump sock, means attaching the upper portion of the prosthetic limb directly to the exterior of the stump sock, and a lower pylon attached to the bottom of the cup-shaped upper portion of the prosthetic limb.

6. A stump sock according to claim 1 attached to a temporary prosthetic limb having a cup-shaped upper portion surrounding the temporary stump sock and in direct contact with the exterior of the stump sock, means attaching the upper portion of the prosthesis directly to the exterior of the stump sock, and a lower pylon attached to the bottom of the cup-shaped upper portion of the prosthesis.

7. A permanent stump sock comprising a flexible, resilient composite material comprising a base layer of a flexible, resilient elastomeric material, and first and second layers of a flexible and stretchable protective fabric adhered to opposite sides of the elastomeric base layer, the composite material being cut, overlaid and seamed to form a tubular sock which is open at its top, closed at its bottom and shaped to generally conform to the shape of an amputee's stump.

8. A stump sock according to claim 7, in which the elastomeric base layer comprises open cell sponge rubber.

9. A stump sock according to claim 8, in which the first and second layers each comprise a fabric having different stretchability in mutually orthogonal directions.

10. A stump sock according to claim 9, in which the elasticity of at least the first or second layer is greater in a lateral direction than in the longitudinal direction with respect to the length of the finished stump sock.

11. Apparatus according to claim 10 in which each layer of the composite material is porous to air and water.

12. A stump sock according to claim 1, in which the base layer of open cell material comprises a resilient foam material having a density of at least about six pounds per cubic inch.

13. A stump sock according to claim 12, in which the foam has an uncompressed uniform layer of thickness of at least about one-fourth inch.

14. A stump sock according to claim 1, in which the resilient open cell base layer comprises a high density foam material.

15. A stump sock according to claim 14, in which the foam material has a density of at least about six pounds per cubic inch and an uncompressed uniform layer thickness of at least about one-fourth inch.

16. A stump sock according to claim 14, in which the inner layer is velour.

17. A stump sock according to claim 16, in which the outer layer is a flexible and stretchable cloth.

18. A stump sock according to claim 14, in which the outer layer is a flexible and stretchable cloth.

19. A stump sock according to claim 1, in which the outer layer is a flexible and stretchable cloth.

20. A stump sock according to claim 7, in which the elastomeric base layer comprises a closed cell material.

21. A stump sock according to claim 20, in which the closed cell material is neoprene rubber.

22. A stump sock according to claim 7, in which the flexible and stretchable inner and outer layers comprise a knitted fabric.

23. A stump sock according to claim 7, in which the elastomeric base layer is between ⅛ and 3/16 inch thick.

24. A temporary post-operative stump sock comprising a flexible, resilient composite material including a base layer of a flexible, resilient high density open cell material; a skin-protecting first layer of a soft, flexible porous material overlying and adhered to a first face of the base layer; and a flexible and stretchable second layer of a protective fabric overlying and adhered to a second face of the base layer, in which each of said layers of the composite material is porous to air and water, the composite material being formed as a tubular sock which is open at its top, closed at its bottom, and shaped generally to conform to the shape of an amputee's stump, with the skin-protecting first layer on the inside of the sock and the protective second layer on the outside of the sock.

25. A stump sock according to claim 24, in which the high density foam material has a density of at least about six pounds per cubic inch and the foam has an uncompressed uniform layer thickness of at least about ¼ inch.

26. A stump sock according to claim 24, in which the protective second layer thereof comprises a fabric with differing levels of elasticity in mutually orthogonal directions, the elasticity being greater in a lateral direction than in the longitudinal direction with respect to the length of the finished stump sock.

27. A permanent stump sock comprising a flexible, resilient composite material comprising a base layer of a flexible, cellular, resilient elastomeric material, and first and second layers of a flexible and stretchable protective fabric adhered to opposite sides of the elastomeric base layer, the composite material being formed as a tubular sock which is open at its top, closed at its bottom, and shaped to generally conform to the shape of an amputee's stump.

28. A stump sock according to claim 27, in which the elastomeric base layer comprises an open cell sponge layer.

29. A stump sock according to claim 27, in which the elastomeric base layer comprises a closed cell material.

30. A stump sock according to claim 27, in which the first and second layers each comprise a fabric having different stretchability in mutually orthogonal directions, and in which the elasticity of at least one of the first or second layers is greater in a lateral direction than in the longitudinal direction with respect to the length of the finished stump sock.

31. A stump sock according to claim 27, in which the elastomeric base layer comprises neoprene rubber, and the first and second layers comprise a knitted fabric.

* * * * *